(12) United States Patent
Harada (10) Patent No.: US 6,980,293 B1
(45) Date of Patent: Dec. 27, 2005

(54) IMMERSION MEDIUM SUPPLY APPARATUS, FLUORESCENCE SPECTROMETRY INSPECTION APPARATUS, AND CULTURE MICROSCOPE

(75) Inventor: Mitsuo Harada, Hachioji (JP)

(73) Assignee: Olympus Optical Co., Ltd., Tokyo (JP)

(*) Notice: Subject to any disclaimer, the term of this patent is extended or adjusted under 35 U.S.C. 154(b) by 364 days.

(21) Appl. No.: 10/458,697

(22) Filed: Jun. 9, 2003

(30) Foreign Application Priority Data

Jun. 11, 2002 (JP) .............................. 2002-170386

(51) Int. Cl.[7] .............................................. G01J 3/30
(52) U.S. Cl. ...................................... 356/317; 356/246
(58) Field of Search ............................. 356/317, 318, 356/244–246; 435/286.1, 287.1, 288.5, 288.7

(56) References Cited

U.S. PATENT DOCUMENTS 4,734,372 A * 3/1988 Rotman ........................ 435/29
4,974,952 A * 12/1990 Focht ......................... 359/398
6,388,746 B1 * 5/2002 Eriksson et al. ............. 356/318
6,727,089 B2 * 4/2004 Ho et al. .................. 435/288.3

FOREIGN PATENT DOCUMENTS

| JP | 60-156521 U | 10/1985 |
| JP | 3-25598 Y2 | 6/1991 |
| JP | 7-3611 U | 7/1995 |
| JP | 2001-502062 A | 2/2001 |

* cited by examiner

Primary Examiner—Layla G. Lauchman
(74) Attorney, Agent, or Firm—Frishauf, Holtz, Goodman & Chick, P.C.

(57) ABSTRACT

An immersion medium supply apparatus has an immersion medium which is filled between an observation sample and a liquid immersion objective, a temperature control unit which controls the immersion medium to a predetermined temperature, and an immersion medium supply unit which supplies the liquid immersion objective with the immersion medium controlled at the predetermined temperature by the temperature control unit.

17 Claims, 4 Drawing Sheets

IMMERSION MEDIUM SUPPLY APPARATUS, FLUORESCENCE SPECTROMETRY INSPECTION APPARATUS, AND CULTURE MICROSCOPE

CROSS-REFERENCE TO RELATED APPLICATIONS

This application is based upon and claims the benefit of priority from the prior Japanese Patent Application No. 2002-170386, filed Jun. 11, 2002, the entire contents of which are incorporated herein by reference.

BACKGROUND OF THE INVENTION

1. Field of the Invention

The present invention relates to an immersion medium supply apparatus which supplies an immersion medium to a liquid immersion objective, a fluorescence spectrometry inspection apparatus, and a culture microscope.

2. Description of the Related Art

It is well known that the reaction of a biological sample such as protein is largely influenced by a change in temperature. There are various ideas for keeping a sample at a predetermined temperature when observing such a biological sample.

Jpn. UM Appln. KOKAI Publication No. 60-156521 discloses one of the technologies to realize the idea of keeping the temperature of a specimen constant by providing a heating element or an electric heating plate in a stage, and heating a specimen set in a glass laboratory dish and placed on the stage by such a heating element or an electric heating plate.

Jpn. UM Appln. KOKAI Publication No. 7-36118 discloses another technology to control a sample temperature constant by providing a pipe to supply water controlled to an appropriate temperature around a sample and an objective, and flowing water at a predetermined temperature in the pipe. Further, as disclosed by Jpn. UM Appln. KOKOKU Publication No. 3-25598, it is also well known to provide a heating means in a heat retaining box of a solvent observation container placed on a mounting table constructed partially of a heating body, to control the solvent sample in the solvent observation container to an appropriate heat retaining state.

Recently, as disclosed by PCT National Publication No. 2001-502062, there has been considered an inspection method for specifying the reaction of a biological molecule by catching the motion of a fluorescent labeled molecule floating in a micro area in liquid by fluorescence microscope photometry.

This method uses a sample vessel called a micro plate having many wells for inspection, which is made of resin or uses a cover glass at the bottom. A fluorescent labeled sample is put in each well of the micro plate, the fluorescence from the fluorescent labeled sample is detected by a micro plate reader, the intensity of fluctuation radiated from the sample is monitored, and the sample is analyzed. In this case, the sample in the well of the micro plate is in the state where small and large molecules are floating in the liquid. Excitation light is condensed at the floating molecule by a liquid immersion objective through the cover glass at the bottom of the micro plate, the excited fluorescence is detected by the molecule resolution, and the molecule nature is determined by a computation.

BRIEF SUMMARY OF THE INVENTION

According to a first aspect of the present invention, there is provided an immersion medium supply apparatus comprising an immersion medium which is filled between an observation sample and a liquid immersion objective, a temperature control unit which controls the immersion medium to a predetermined temperature, and an immersion medium supply unit which supplies the liquid immersion objective with the immersion medium controlled the temperature by the temperature control unit.

According to a second aspect of the present invention, there is provided a fluorescence spectrometry inspection apparatus comprising a liquid immersion objective which condenses the light from a sample of a fluorescent labeled biological molecule floating in liquid, an immersion medium which is filled between the sample and the liquid immersion objective, an optical system which is provided with a photodetector and a fluorescent illumination to detect a magnified image of at least the liquid immersion objective, an arithmetic unit which calculates the motion of the sample according to the output of the photodetector, a monitor which displays the calculation result by the arithmetic unit, a temperature control unit which controls the immersion medium to a predetermined temperature, and an immersion medium supply unit which supplies the immersion medium lens with the immersion medium controlled the temperature by the temperature control unit.

According to a third aspect of the present invention, there is provided a culture microscope comprising a culture vessel which contains a stage on which an observation sample is placed, a microscope which supports the stage, a liquid immersion objective which is supported by the microscope, and an image pickup unit and optics which capture a magnified image of the observation sample set in the microscope; an immersion medium which is filled between the observation sample and the liquid immersion objective; a temperature control unit which controls the immersion medium to a predetermined temperature; an immersion medium supply unit which supplies the immersion medium lens with the immersion medium controlled the temperature by the temperature control unit; and an warm air circulator which feeds warm air to the culture vessel.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, embodiments of the present invention will be explained with reference to the accompanying drawings.

First Embodiment

Figure 1:
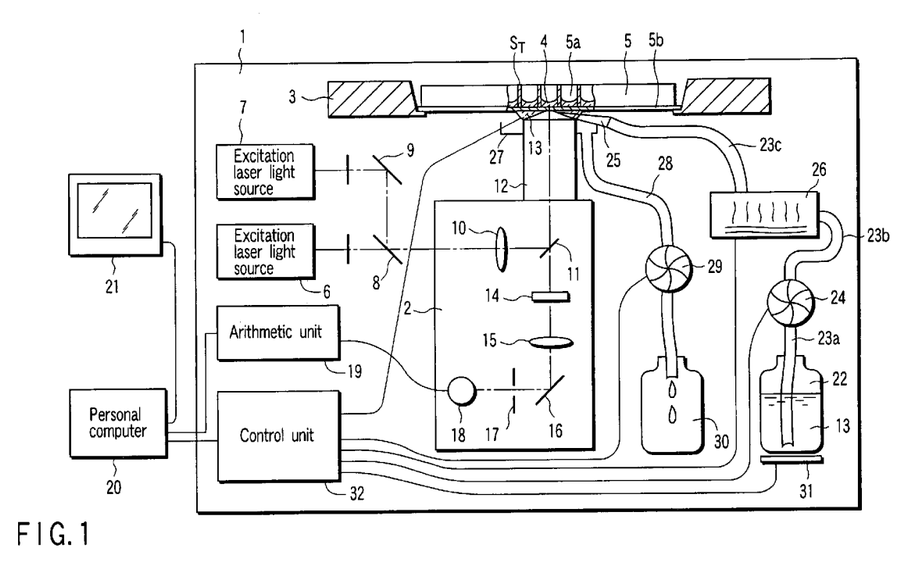
FIG. 1 is a view showing a schematic block diagram of a first embodiment of the present invention.

FIG. 1 shows a schematic block diagram of an inspection apparatus to which an immersion medium supply apparatus of the present invention is applied. In FIG. 1, an inverted microscope 2 is provided in an apparatus body 1.

In the inverted microscope 2, a XY stage 3 is provided. On the XY stage 3, a micro plate 5 having many wells 5a to contain a sample 4 is mounted.

Figure 3:
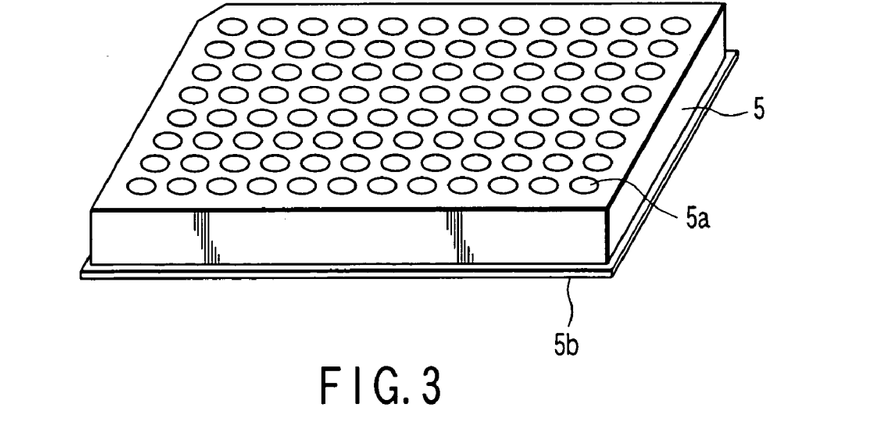
FIG. 3 is a view showing a schematic configuration of a micro plate used in the first embodiment.

The micro plate 5 is a resign-made sample vessel, having many wells 5a arranged to contain a sample 4, as shown in FIG. 3. At the bottom of the micro plate 5, a cover glass 5b with the thickness of about 0.17 mm is provided as a transparent member. Thus, each well 5a of the micro plate 5 has the structure that the cover glass 5b is glued to the bottom to be suitable for inverted observation from the bottom side. The sample 4 to be put into the well 5a is in the state that a fluorescent labeled biological molecule is colloidal and floating in the liquid.

Figure 2:
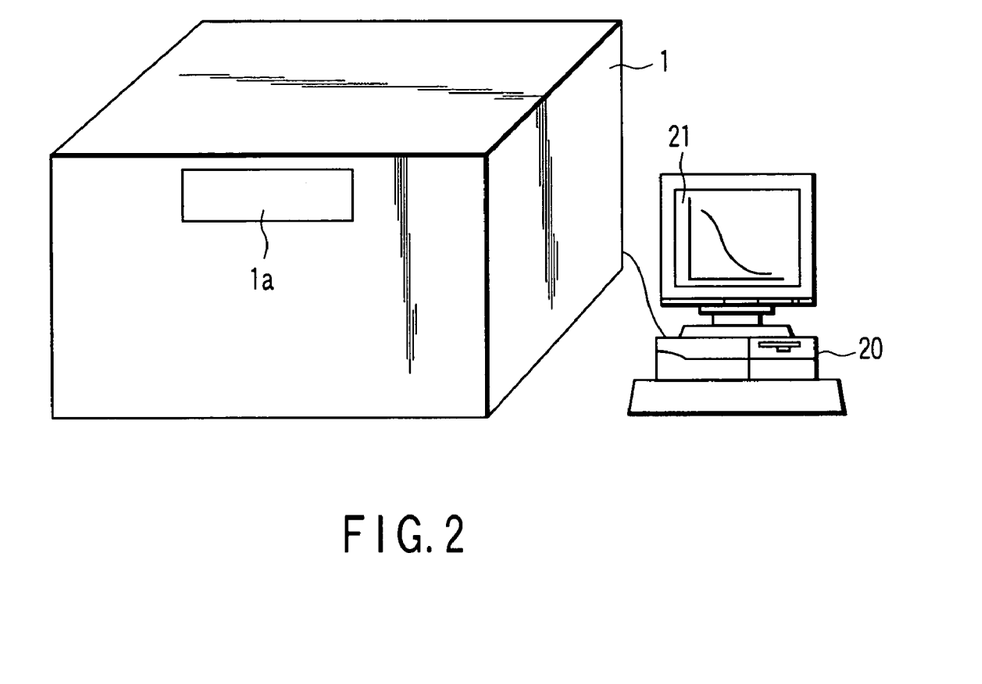
FIG. 2 is an illustration showing an external view of a main unit of the first embodiment.

In the front of the apparatus body 1, there is provided a micro plate insertion window 1a, as shown in FIG. 2. The micro plate insertion window 1a is a window to insert and remove the micro plate 5 into/from the apparatus body 1. When the micro plate 5 is inserted into the apparatus body 1 through the micro plate insertion window 1a, the plate is placed on the XY stage 3 and the sample can be automatically inspected in this state.

Laser beams from excitation laser light sources 6, 7 with different wavelengths are selectively or simultaneously guided to an inverted microscope 2 through a half-mirror 8 and a mirror 9. The laser beams are paralleled by a collimator lens 10, reflected by a dichroic mirror 11, and guided to an objective 12.

In this case, the objective 12 uses a liquid immersion object lens with the condensing ability increased to be able to condense a light beam in a micro area of several micrometers in the liquid of the sample 4 (a water immersion objective in the example shown in the drawing)(hereinafter, explained as a water immersion objective 12). The water immersion objective 12 is located close to the cover glass 5b at the bottom of the micro plate 5. The immersion medium (pure water) 13 is filled between the water immersion objective 12 and the cover glass 5b.

The excitation light passing through the water immersion objective 12 advances to the well 5a of the micro plate 5 through the immersion medium 13 and cover glass 5b, and is condensed in a micro area in the liquid of the sample 4. When a fluorescent labeled biological molecule floating in the liquid of the sample 4 exists in the micro area condensed by the excitation light, it emits fluorescence at that moment.

This fluorescence passes the water immersion objective 12, dichroic mirror 11 and excitation barrier filter 14, and goes into an image forming lens 15, where the magnified image of the fluorescence is formed by the water immersion objective 12. The fluorescence is then turned by a reflecting mirror 16, passes through a pinhole 17, and reaches a photodetector 18.

In this case, the fluorescent labeled biological molecule floating in the liquid of the sample 4 is a colloidal floating body, and it is vibrated by Brownian motion, and goes in and out from the micro area. Thus, the photodetector 18 detects the fluorescence of the biological molecule going in and out from the micro area.

The photodetector 18 is connected to an arithmetic unit 19. The arithmetic unit 19 calculates the fluctuation in the detection signal of the photodetector.

The arithmetic unit 19 is connected to a personal computer 20 as a central processing means provided in the apparatus body 1. The personal computer 20 analyzes the nature of the biological molecule depending on the fluctuation calculated by the arithmetic unit 19, and displays the result in a display unit 21.

The water immersion objective 12 is provided with an immersion medium supply apparatus of the present invention explained as follows.

Figure 4:
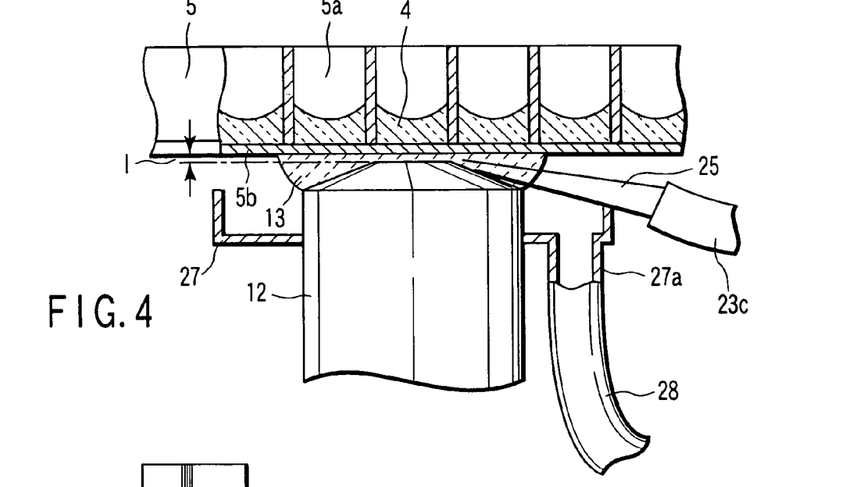
FIG. 4 is a magnified view showing the structure between a water immersion objective and a cover glass of the micro plate of the first embodiment.

In this case, the immersion medium (pure water) 13 is filled in a gap between the water immersion objective 12 and the cover glass 5b at the bottom of the micro plate 5. The immersion medium 13 is prepared in a water supply bottle 22 as an immersion medium supply source. The water supply bottle 22 is provided with a water supply pipe 23a, a water supply pump 24, water supply pipes 23b, 23c, and a liquid supply nozzle (water supply nozzle) 25, constituting an immersion medium supply means. The immersion medium 13 in the water supply bottle 22 is sent to the water supply pump 24 through the water supply pipe 23a. The immersion medium 13 is supplied from the water supply nozzle 25 to the gap between the water immersion objective 12 and the cover glass 5b, through the water supply pipes 23b, 23c. In this case, as shown in FIG. 4, a distance I between the cover glass 5b and the forward end of the water immersion objective 12 is very small, 1 mm or less, for example. Thus, the immersion medium 13 supplied to this gap is held there by the surface tension. Between the water supply pipes 23b and 23c, a temperature control unit 26 is provided as a temperature control means. The temperature control unit 26 heats or cools the immersion medium 13 to a predetermined temperature. After the temperature is adjusted by the temperature control unit 26, the immersion medium 13 is supplied to the water supply nozzle 25.

At the forward end of the water immersion objective 12, a liquid receiver 27 is provided. The liquid receiver 27 is provided along the circumference of the water immersion objective 12, as shown in FIG. 4, to receive the immersion medium 13 that cannot be held in the gap between the water immersion objective 12 and the cover glass 5b. The liquid receiver 27 is provided with a drain outlet 27a. The drain outlet 27a is provided with a drain pipe 28, a drain pump 29 and a drain bottle 30, constituting a immersion medium draining means. The drain outlet can send the immersion medium 13 received by the liquid receiver 27 to the drain pump 29 through the drain pipe 28, and collect it in the drain bottle 30.

A control unit 32 is connected to the water supply pump 24, temperature control unit 26 and drain pump 29. The control unit 32 controls the operations of the water supply pump 24, temperature control unit 26 and drain pump 29, according to the instructions from the personal computer 20.

The water supply bottle 22 and drain bottle 30 are provided in the apparatus body 1, but they are arranged to be easily replaced from the outside of the apparatus body 1, and to supply the immersion medium 13 to the water supply bottle 22. Of course, if the water supply bottle 22 and drain bottle 30 are located outside of the apparatus body 1, it becomes more easy to replace the water supply bottle 22 and drain bottle 30, and to supply the immersion medium 13 to the water supply bottle 22.

In the above-mentioned configuration, first prepare the micro plate 5 containing the fluorescent labeled sample 4 in many wells 5a. Insert the micro plate 5 into the apparatus body 1 through the micro plate insertion window 1a, and place it on the XY stage 3.

When the XY stage 3 is moved and the first well 5a is positioned on the optical axis of the water immersion objective 12 in this state, the immersion medium 13 prepared in the water supply bottle 22 is sent to the water supply pump 24 through the water supply pipe 23a, and supplied by the water supply nozzle 25 to the gap between the water immersion objective 12 and the cover glass 5b, through the water supply pipes 23b and 23c. In this case, the immersion medium 13 is held there by the surface tension.

At this time, the immersion medium 13 is controlled to a predetermined temperature by the temperature control unit 26. Thus, when the immersion medium 13 comes in contact with the cover glass 5b, the sample 4 is controlled to a predetermined temperature by the heat exchange between the immersion medium 13 and the cover glass 5b, and the heat exchange between the cover glass 5b and the sample 4. In this case, the cover glass 5b uses a glass with the thickness of about 0.17 mm, and the heat capacity is made small compared with the surrounding materials. Thus, the heat exchange with the sample 4 is not interrupted, and contrarily the heat conductivity increases and makes the heat exchange efficient.

In this state, the above-mentioned fluorescence detection is executed, the fluorescence of the biological molecule floating in the liquid of the sample 4 is detected by the photodetector 18, the nature of the biological molecule is analyzed by the personal computer 20 based on the fluctuation calculated by the arithmetic unit 19, and the result is displayed in the display unit 21.

When inspection of the first sample 4 is finished, the XY stage 3 is moved, the next well 5a is positioned on the optical axis of the water immersion objective 12, and the fluorescence detection is executed in the same way.

In this case, if the cover glass 5b moves with respect to the water immersion projective 12 as the XY stage 3 moves, the immersion medium 13 that cannot be held between the water immersion objective 12 and the cover glass 5b drops, and the immersion medium 13 is received by the liquid receiver 27 provided around the water immersion objective 12. The immersion medium 13 is sent from the drain outlet 27a to the drain pipe 28, and collected in the drain bottle 30 by the drain pump 29. At the same time, a certain quantity of immersion medium 13 is supplied from the water supply nozzle 25 to the gap between the water immersion objective 12 and the cover glass 5b.

It is allowed to supply the immersion medium 13 to the gap between the water immersion objective 12 and the cover glass 5b by certain quantities at every predetermined time.

Thereafter, in the same way, the fluorescence detection is executed for all wells 5a of the micro plate 5, and the analysis result is displayed in the display unit 21 by the personal computer 20.

Therefore, according to the above-mentioned embodiment, considering the immersion medium 13 used in the water immersion objective 12, the immersion medium 13 to be filled in the gap between the water immersion objective 12 and the cover glass 5b is adjusted to a predetermined temperature and supplied, and the temperatures of all samples 4 put in the wells 5a of the micro plate 5 can be controlled to the adjusted predetermined temperature of the immersion medium 13. This makes it possible to hold constant the Brownian motion whose momentum is changed by the motion of the floating molecule in the liquid of the sample 4, that is, a temperature change, and stable detection of fluorescence is possible for the sample 4 in all wells 5a of the micro plate 5. Namely, in observation of a biological sample, a suitable form can be observed, and stable data can be obtained and right judgment is possible in fluorophotometry to catch the molecule motion.

As an inspection method, fluorescence correlation spectroscopy is available, and the information concerning the diffusion intensity and the number of molecules can be obtained by analyzing the fluctuation in the fluorescence intensity. This apparatus is used in a fluorescence molecule inspection apparatus such as fluorescence correlation spectroscopy.

The temperature control range is 0–100° C. maximum, due to use of pure water. For example, the temperature is about 25° C. for saltwater creatures using seawater, 37° C. for the living state of a biological cell such as animal protein, and 80° C. for DNA. The temperature range for the living state of a biological cell is desirably 37±1° C. The temperature accuracy is to be selected depending on the inspection object and the object temperature sensitivity.

Further, by setting much quantity of the immersion medium 13 supplied to the gap between the water immersion objective 12 and the cover glass 5b, stable temperature control of the sample 4 is possible. By repeating frequently the supply and drain of the immersion medium 13, the temperature control of the sample 4 can be easily changed, and accurate temperature control is also possible.

Further, the temperature of the immersion medium 13 is controlled by utilizing the immersion medium 13 used for the water immersion objective 12, and the whole apparatus structure can be made simple, and the price can be lowered.

In the above-mentioned embodiment, the temperature control unit 26 is provided between the water supply pipes 23b and 23c, but it is possible instead of or at the same time of this arrangement to provide a bottle temperature control unit 31 which controls the temperature of the whole water supply bottle 22, close to the water supply bottle 22.

It is further possible to provide a sensor ST which always detects the temperature of the immersion medium 13 held between the water immersion objective 12 and the cover glass 5b, and control the temperature control unit 26 by the output of the sensor ST so that the immersion medium 13 between the water immersion objective 12 and the cover glass 5b is always kept at a predetermined temperature.

Further, in the above-mentioned embodiment, the immersion medium 13 of the water supply bottle 22 is supplied to the gap between the water immersion objective 12 and the cover glass 5b, and the residual immersion medium 13 is collected in the drain bottle 30, but it is allowed to circulate the immersion medium 13 supplied between the water immersion objective 12 and the cover glass 5b. In this case, a foreign matter may mix into the immersion medium 13 during circulation of the immersion medium 13, and it is necessary to eliminate the foreign matter completely by using a filter or the like.

Further, considering that the temperature in the apparatus body 1 is several degrees higher than the outside temperature, it is also permitted to provide a heat exchanger instead of the temperature control unit 26 to control the immersion medium 13 to the same temperature as the temperature in the apparatus body, and supply the temperature controlled immersion medium to the gap between the water immersion lens 12 and the cover glass 5*b*.

Further, in the above-mentioned embodiment, an example of water immersion type using pure water in the immersion medium 13 has been described, but an oil immersion type using oil is also applicable.

The water supply nozzle 25, which supplies the immersion medium 13 to the gap between the water immersion objective 12 and the cover glass 5*b*, is removably held outside of the water immersion objective 12. The water supply nozzle 25 may be embedded in the outer frame of the water immersion objective 12. The water supply nozzle 25 may also be held by the inverted microscope 2, or may be held by the liquid receiver 27 provided around the forward end of the water immersion objective. Only one water supply nozzle 25 is shown in the drawing, but three, five or more nozzles can be used.

Modification of First Embodiment

A modification of the first embodiment of the present invention will be explained.

This modification shows an example of applying the immersion medium supply unit of the first embodiment of the present invention, to an inverted microscope.

Figure 5:
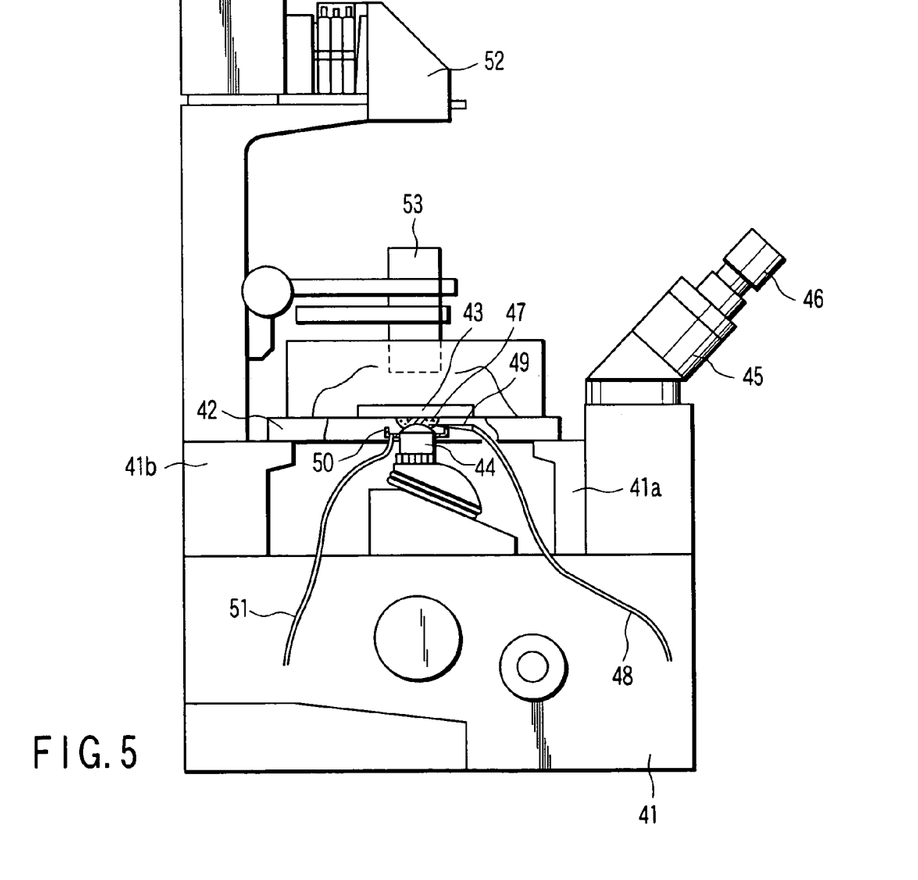
FIG. 5 is a view showing a schematic configuration of a modification of the first embodiment of the present invention.

FIG. 5 shows a schematic configuration of a modification of the first embodiment.

In FIG. 5, a stage 42 is provided on a front fixing unit 41*a* and a rear fixing unit 41*b* of a microscope body 41.

A laboratory dish sample 43 is placed on the stage 42. The laboratory dish sample 43 has a cover glass at the bottom, and a biological sample is put in the dish.

A luminous flux from a not-shown reflected light source is radiated to the biological sample from the bottom (cover glass) side of the laboratory dish sample 43 through a water immersion objective 44. The light from the laboratory dish sample 43 is relayed by a not-shown relay optics through the water immersion objective 44, and applied to an eyepiece 46 fit to an observation tube 45, for visual observations.

In this case, also, an immersion medium (pure water) 47 is filled in the gap between the water immersion objective 44 and the cover glass at the bottom of the laboratory dish sample 43. The immersion medium 47 is, like the one shown in FIG. 1, controlled to a predetermined temperature by a not-shown temperature control unit, and supplied from a water supply pipe 49 to the gap between the water immersion objective 44 and the cover glass, through the water supply pipe 48, and held there by the surface tension. The immersion medium 47 that cannot be held between the objective 44 and the cover glass is drained from a drain pipe 51 through a liquid receiver 50.

In this case, the immersion medium 47 may be supplied by either electrically or manually using a pump.

Further, a transmitted light source 52 and a condenser lens 53 are also shown in FIG. 5.

According to this modification, the immersion medium 47 can be adjusted to a predetermined temperature and filed in the gap between the water immersion objective 44 and the cover glass at the bottom of the laboratory dish sample 43, and the temperature of the laboratory dish sample 43, or the biological sample put in a laboratory dish, can be controlled to a predetermined temperature, enabling observations of a high quality biological sample.

Second Embodiment

A second embodiment of the present invention will be explained hereinafter.

Figure 6:
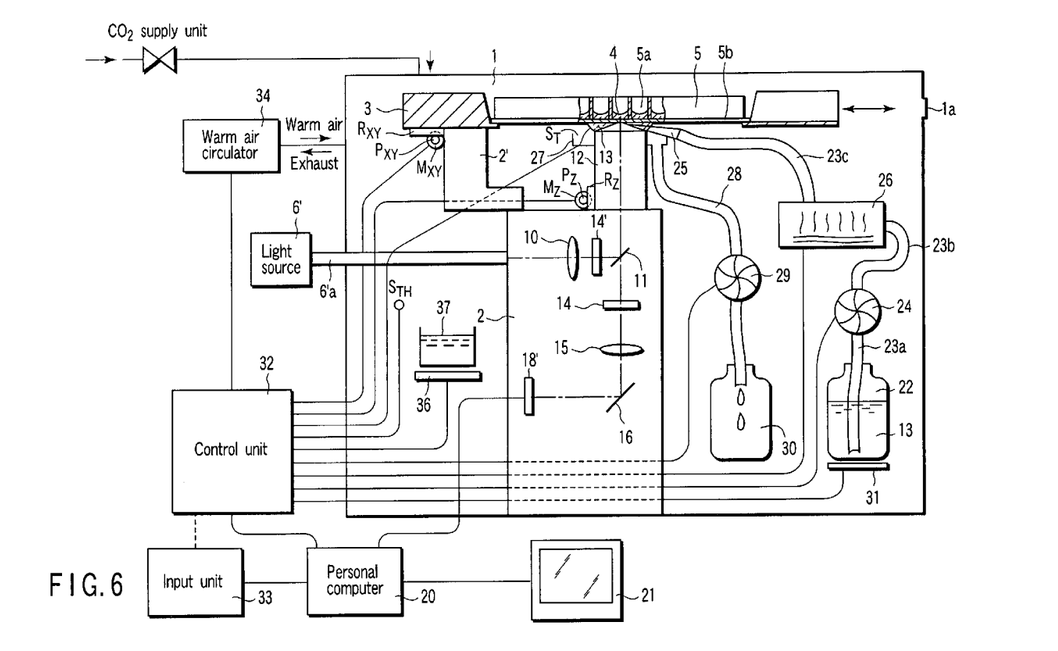
FIG. 6 is a view showing a schematic configuration of a second embodiment of the present invention.

FIG. 6 shows a schematic configuration of a culture microscope to which an immersion medium supply apparatus of the present invention is applied. In FIG. 6, the same reference numerals are given to the same components as those in the first embodiment.

In FIG. 6, an inverted microscope 2 is provided in an apparatus body 1. In the inverted microscope 2, a XY stage 3 is provided through a stage mount 2'. On the XY stage 3, a rack $R_{XY}$, a pinion $P_{XY}$ and a drive motor $M_{XY}$ are provided. On the XY stage 3, a micro plate 5 having many wells 5*a* to contain a sample 4 is mounted.

The micro plate 5 is a resign-made sample vessel, having many wells 5*a* arranged to contain a sample 4, as shown in FIG. 3. At the bottom of the micro plate 5, a cover glass 5*b* with the thickness of about 0.17 mm is provided as a transparent member. Thus, each well 5*a* of the micro plate 5 has the structure that the cover glass 5*b* is glued to the bottom to be suitable for inverted observation from the bottom side. The sample 4 to be put into the well 5*a* is in the state that a fluorescent labeled biological molecule is living in culture liquid.

In the front of the apparatus body 1, there is provided a micro plate insertion window 1*a*, as shown in FIG. 2. The micro plate insertion window 1*a* is a window to insert and remove the micro plate 5 into/from the apparatus body 1. When the micro plate 5 is inserted into the apparatus body 1 through the micro plate insertion window 1*a*, the plate is placed on the XY stage 3 and the sample can be automatically inspected in this state.

The illumination light from a light source 6' is guided to the inverted microscope 2. The illumination light passes through an excitation light exciter filter 14' and a lens 10', and is reflected by a dichroic mirror 11 and guided to an objective 12.

In this case, the objective 12 uses a liquid immersion object lens with the condensing ability increased to be able to condense a light beam to a biological cell in the sample 4 (a water immersion objective in the example shown in the drawing)(hereinafter, explained as a water immersion objective 12). The water immersion objective 12 is located close to the cover glass 5*b* at the bottom of the micro plate 5. The immersion medium (pure water) 13 is filled between the water immersion objective 12 and the cover glass 5*b*.

The excitation light passing through the water immersion objective 12 advances to the well 5*a* of the micro plate 5 through the immersion medium 13 and cover glass 5*b*, and is condensed to a biological molecule in the liquid of the sample 4. When a fluorescent labeled biological molecule in the liquid of the sample 4 exists in the area of the excitation light, it emits fluorescence.

This fluorescence passes the water immersion objective 12, dichroic mirror 11 and excitation barrier filter 14, and goes into an image forming lens 15, where the magnified image of the fluorescence is formed by the water immersion objective 12. The fluorescence is then turned by a reflecting mirror 16, and reaches an image pickup element 18' such as a solid image pickup element (CCD). As the water immersion objective 12 moves up and down between the inverted microscope 2, a rack $R_Z$ is provided in the water immersion objective 12, and a pinion $P_Z$ and a motor $M_Z$ are provided in the inverted microscope.

In this case, the fluorescent labeled biological cell in the liquid of the sample 4 is magnified by the water immersion objective 12, and the image pickup element 18' takes the fluorescence image of the biological cell.

The image pickup element 18' is connected to a personal computer 20 as a central processing means provided in the apparatus body 1. The personal computer 20 is connected to a display unit 21 such as a monitor and an input unit 33 such as a keyboard.

The water immersion objective 12 is provided with an immersion medium supply apparatus of the present invention as explained below.

In this case, the immersion medium (pure water) 13 is filled in a gap between the water immersion objective 12 and the cover glass 5b at the bottom of the micro plate 5. The immersion medium 13 is prepared in a water supply bottle 22 as an immersion medium supply source. The water supply bottle 22 is provided with a water supply pipe 23a, a water supply pump 24, water supply pipes 23b, 23c, and a liquid supply nozzle (water supply nozzle) 25, constituting an immersion medium supply means. The immersion medium 13 in the water supply bottle 22 is sent to the water supply pump 24 through the water supply pipe 23a. The immersion medium 13 is supplied from the water supply nozzle 25 to the gap between the water immersion objective 12 and the cover glass 5b, through the water supply pipes 23b, 23c. In this case, as shown in FIG. 4, a distance I between the cover glass 5b and the forward end of the water immersion objective 12 is very small, 1 mm or less, for example. Thus, the immersion medium 13 supplied to this gap is held there by the surface tension. Between the water supply pipes 23b and 23c, a temperature control unit 26 is provided as a temperature control means. The temperature control unit 26 heats or cools the immersion medium 13 to a predetermined temperature. After the temperature is adjusted by the temperature control unit 26, the immersion medium 13 is supplied to the water supply nozzle 25.

At the forward end of the water immersion objective 12, a liquid receiver 27 is provided. The liquid receiver 27 is provided along the circumference of the water immersion objective 12, as shown in FIG. 4, to receive the immersion medium 13 that cannot be held in the gap between the water immersion objective 12 and the cover glass 5b. The liquid receiver 27 is provided with a drain outlet 27a. The drain outlet 27a is provided with a drain pipe 28, a drain pump 29 and a drain bottle 30, constituting a immersion medium draining means. The drain outlet can send the immersion medium 13 received by the liquid receiver 27 to the drain pump 29 through the drain pipe 28, and collect it in the drain bottle 30.

A control unit 32 is connected to the water supply pump 24, temperature control unit 26 and drain pump 29. The control unit 32 controls the operations of the water supply pump 24, temperature control unit 26 and drain pump 29, according to the instructions from the personal computer 20. Further, the control unit 32 is connected to a thermocouple type medium temperature sensor $S_T$, which is provided in the immersion medium 13 and fixed to the water immersion objective 21. The temperature of the medium temperature sensor $S_T$ is fed back to the control unit 32, to control the temperature of the temperature control unit 26.

The water supply bottle 22 and drain bottle 30 are provided in the apparatus body 1, but they are arranged to be easily replaced from the outside of the apparatus body 1, and to supply the immersion medium 13 to the water supply bottle 22. Of course, if the water supply bottle 22 and drain bottle 30 are located outside of the apparatus body 1, it becomes more easy to replace the water supply bottle 22 and drain bottle 30, and to supply the immersion medium 13 to the water supply bottle 22.

Further, a warm air circulator 34 and a carbonic acid ($CO_2$) supply unit are provided outside of the apparatus body 1. A humidify water 37 and a heater 36 to heat it are provided outside of the apparatus body 1. The control unit 32 is connected to the warm air circulator 34 and heater 36. The control unit 32 is connected to a thermocouple type temperature/humidity sensor $S_{TH}$ provided in the apparatus body 1.

In the above-mentioned configuration, first prepare the micro plate 5 containing the fluorescent labeled sample 4 in many wells 5a. Insert the micro plate 5 into the apparatus body 1 through the micro plate insertion window 1a, and place it on the XY stage 3.

When the XY stage 3 is moved and the first well 5a is positioned on the optical axis of the water immersion objective 12 in this state, the immersion medium 13 prepared in the water supply bottle 22 is sent to the water supply pump 24 through the water supply pipe 23a, and supplied by the water supply nozzle 25 to the gap between the water immersion objective 12 and the cover glass 5b, through the water supply pipes 23b and 23c. In this case, the immersion medium 13 is held there by the surface tension.

At this time, the immersion medium 13 is controlled to a predetermined temperature by the temperature control unit 26. Thus, when the immersion medium 13 comes in contact with the cover glass 5b, the sample 4 is controlled to a predetermined temperature by the heat exchange between the immersion medium 13 and the cover glass 5b, and the heat exchange between the cover glass 5b and the sample 4. In this case, the cover glass 5b uses a glass with the thickness of about 0.17 mm, and the heat capacity is made small compared with the surrounding materials. Thus, the heat exchange with the sample 4 is not interrupted, and contrarily the heat conductivity increases and makes the heat exchange efficient.

The PH density of the liquid of the sample 4 is adjusted by the carbon dioxide ($CO_2$) supply apparatus. Because, when $CO_2$ is supplied to the inside of the apparatus body 1, the PH of the sample can be adjusted consequently.

The humidify water 37 heated by the heater 36 is controlled by feeding back the value of the temperature/humidity sensor $S_{TH}$ before the humidity is saturated (100%), preventing the sample 4 from drying.

By being controlled by the warm air circulator 34 by feeding back the value of the temperature/humidity sensor $S_{TH}$, the inverted microscope 2, stage mount 2' and XY stage 3 are controlled to a temperature almost the same as the temperature of the immersion medium 13. In an example of biological cell, the temperature is kept at 37±1° C.

In this state, the above-mentioned fluorescence observation is executed, the fluorescence of the biological cell in the liquid of the sample 4 is picked up as an image by the image pickup element 18', and the biological cell is displayed in the display unit 21 through the personal computer 20.

When inspection of the first sample 4 is finished, the XY stage 3 is moved, the next well 5a is positioned on the optical axis of the water immersion objective 12, and the fluorescence observation is executed in the same way.

In this case, if the cover glass 5b moves with respect to the water immersion projective 12 as the XY stage 3 moves, the immersion medium 13 that cannot be held between the water immersion objective 12 and the cover glass 5*b* drops, and the immersion medium 13 is received by the liquid receiver 27 provided around the water immersion objective 12. The immersion medium 13 is sent from the drain outlet 27*a* to the drain pipe 28, and collected in the drain bottle 30 by the drain pump 29. At the same time, a certain quantity of immersion medium 13 is supplied from the water supply nozzle 25 to the gap between the water immersion objective 12 and the cover glass 5*b*.

Thereafter, in the same way, the fluorescence observation is executed for all wells 5*a* of the micro plate 5, and the biological cell is displayed in the display unit 21 by the personal computer 20.

The XY motion and focusing of the micro plate 5 are performed by the drive motor $M_{XY}$ for moving the XY and the motor $M_Z$ for focusing from the control unit 32 through the personal computer 20, according to the instruction from the input unit 33. It is also permitted to send the instruction from the input unit 33 directly to the control unit 32.

Therefore, according to the above-mentioned embodiment, considering the immersion medium 13 used in the water immersion objective 12, the immersion medium 13 to be filled in the gap between the water immersion objective 12 and the cover glass 5*b* is adjusted to a predetermined temperature and supplied, and the temperatures of all samples 4 put in the wells 5*a* of the micro plate 5 can be controlled to the adjusted predetermined temperature of the immersion medium 13. As the temperature of the water immersion objective 12 is set almost the same as the predetermined temperature by the immersion medium 13, the influence of the water immersion objective 12 is minimized. The temperatures of the inverted microscope 2 and sample 4 are kept at predetermined temperatures by the warm air circulator 32, and the temperature of the water immersion objective 12 becomes almost the same as the predetermined temperature.

This makes it possible to keep the biological cell in the liquid of the sample 4 at a constant temperature, and stable fluorescence observation is possible for the sample 4 in all wells 5*a* of the micro plate 5.

Further, by setting much quantity of the immersion medium 13 supplied to the gap between the water immersion objective 12 and the cover glass 5*b*, stable temperature control of the sample 4 is possible. By repeating frequently the supply and drain of the immersion medium 13, the temperature control of the sample 4 can be easily changed, and accurate temperature control is also possible.

In the above-mentioned embodiment, the temperature control unit 26 is provided between the water supply pipes 23*b* and 23*c*, but it is also possible instead of or at the same time of this arrangement to provide a bottle temperature control unit 31 which controls the temperature of the whole water supply bottle 22.

Further, in the above-mentioned embodiment, the immersion medium 13 of the water supply bottle 22 is supplied to the gap between the water immersion objective 12 and the cover glass 5*b*, and the residual immersion medium 13 is collected in the drain bottle 30, but it is allowed to circulate the immersion medium 13 supplied between the water immersion objective 12 and the cover glass 5*b*. In this case, a foreign matter may mix into the immersion medium 13 during circulation of the immersion medium 13, and it is necessary to eliminate the foreign matter completely by using a filter or the like.

Further, considering that the temperature in the apparatus body 1 is several degrees higher than the outside temperature, it is also permitted to provide a heat exchanger instead of the temperature control unit 26 to control the immersion medium 13 to the same temperature as the temperature in the apparatus body, and supply the temperature controlled immersion medium to the gap between the water immersion lens 12 and the cover glass 5*b*.

Further, in the above-mentioned embodiment, an example of water immersion type using pure water in the immersion medium 13 has been described, but an oil immersion type using oil is also applicable.

In the above-mentioned embodiment, use of an inverted microscope is described, but the embodiment is applicable also to an upright microscope. The water immersion type using pure water as immersion medium 47 is described, but the embodiment is applicable also to the oil immersion type using oil.

As described hereinbefore, according to the embodiment of the present invention, there is provided an immersion medium supply apparatus, fluorescence spectrometry inspection apparatus, and a culture microscope, which are simple in the structure and low in the price, and able to stably control the sample temperature by utilizing the immersion medium supplied to the liquid immersion objective.

It is to be noted that the present invention is not restricted to the above-mentioned embodiments, and may be embodied in other specific forms without departing from the essential characteristics.

The following inventions can be extracted from each of the above-mentioned embodiments, for example. The following inventions can be applied independently, or can be combined.

According to a first aspect of the present invention, there is provided an immersion medium supply apparatus comprising an immersion medium which is filled between an observation sample and a liquid immersion objective, a temperature control unit which controls the immersion medium at a predetermined temperature, and an immersion medium supply unit which supplies the liquid immersion objective with the immersion medium controlled the temperature by the temperature control unit. The sample can be controlled at a predetermined temperature by adjusting the immersion medium to a predetermined temperature and supplying the immersion medium to the gap between the liquid immersion objective and the observation sample. This makes it possible to observe an appropriate form when observing a biological sample, for example, and obtain stable data and make correct judgment in the fluorescence photometry to capture the molecule motion.

Further, the temperature of the immersion medium 13 is controlled by utilizing the immersion medium used in the liquid immersion objective, and the whole apparatus structure can be made simple, and the price is low.

In the first aspect, desirable embodiments are as follows.

(1) The immersion medium supply unit has a liquid supply nozzle to supply the immersion medium to the immersion medium supply source and the liquid immersion objective, and the temperature control unit is provided between the immersion medium supply source and the liquid supply nozzle.

(2) The water supply nozzle of the immersion medium supply unit is at least one or more, and is removably held by the liquid immersion objective.

(3) The water supply nozzle is embedded in the outer frame of the liquid immersion objective.

(4) The water supply nozzle is embedded in the liquid receiver provided around the forward end of the liquid immersion objective.

According to a second aspect of the present invention, there is a fluorescence spectrometry inspection apparatus comprising a liquid immersion objective which condenses the light from a sample of a fluorescent labeled biological molecule floating in liquid, an immersion medium which is filled between the sample and the liquid immersion objective, an optical system which is provided with a photodetector and a fluorescent illumination to detect a magnified image of at least the liquid immersion objective, an arithmetic unit which calculates the motion of the sample according to the output of the photodetector, a monitor which displays the calculation result by the arithmetic unit, a temperature control unit which controls the immersion medium at a predetermined temperature, and an immersion medium supply unit which supplies the immersion medium lens with the immersion medium controlled the temperature by the temperature control unit. The arithmetic unit preferably performs operations according to fluorescence correlative spectrometry. By analyzing the fluctuation in the fluorescence intensity, the sample temperature is kept constant when obtaining the information concerning the information about the diffusion speed and information about the number of molecules, and the motion of the floating molecule in the liquid of the sample can be held constant, and stable fluorescence detection is possible for the samples in all wells of the micro plate. In the fluorometry to capture the molecule motion, stable data can be obtained and correct judgment is possible.

In the first and second aspects, it is preferable to further provide a sensor which measures the temperature of the immersion medium. The sensor is preferably located close to the liquid immersion objective.

According to a third aspect of the present invention, there is provided a culture microscope comprising a culture vessel which contains a stage on which an observation sample is placed, a microscope which supports the stage, a liquid immersion objective which is supported by the microscope, and an image pickup unit and optics which capture a magnified image of the observation sample set in the microscope; an immersion medium which is filled between the observation sample and the liquid immersion objective; a temperature control unit which controls the immersion medium at a predetermined temperature; an immersion medium supply unit which supplies the immersion medium lens with the immersion medium controlled the temperature by the temperature control unit; and an warm air circulator which feeds warm air to the culture vessel. It is preferably to further provide a sensor which measures the temperature of the immersion medium and the humidity in the culture vessel. The humidity sensor is preferably located close to the liquid immersion objective. The observation sample and liquid immersion objective are kept at a predetermined temperature by the immersion medium. The inside of the culture unit is kept at a predetermined temperature by the warm air circulator. Accordingly, the microscope and liquid immersion objective are kept at a predetermined temperature. When the liquid immersion objective is kept at a predetermined temperature, the observation sample becomes more stabilized through the immersion medium.

In the first to third aspects, it is preferable to further provide an immersion medium drain unit which drains the immersion medium supplied from the immersion medium supply unit to the liquid immersion objective.

Further, the above-mentioned embodiments include the invention of various steps, and various inventions can be extracted by appropriate combination of the plurality of disclosed components. For example, even if several components are deleted from all components shown in the embodiments, the tasks mentioned in Tasks To Be Solved By The Present Invention can be solved. When the effects mentioned in Effects of The Present Invention can be obtained, the configuration with these components deleted can be extracted as an invention. For example, as described in Second Embodiment, though not particularly indicated in Embodiment, the method of adjusting the inside environment by covering the whole microscope by a box-like means is applicable also to the fluorometer according to the first embodiment.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An immersion medium supply apparatus comprising:
   an immersion medium which is filled between an observation sample and a liquid immersion objective;
   a temperature control unit which controls the immersion medium at a predetermined temperature; and
   an immersion medium supply unit which supplies the liquid immersion objective with the immersion medium controlled at the predetermined temperature by the temperature control unit.

2. The immersion medium supply apparatus according to claim 1, wherein
   the immersion medium supply unit has a liquid supply nozzle to supply the immersion medium to the liquid immersion objective and an immersion medium supply source, and
   the temperature control unit is provided between the immersion medium supply source and the liquid supply nozzle.

3. The immersion medium supply apparatus according to claim 2, wherein the water supply nozzle there is at least one liquid supply nozzle of the immersion medium supply unit, and the at least one liquid supply nozzle is removably held by the liquid immersion objective.

4. The immersion medium supply apparatus according to claim 3, wherein the liquid supply nozzle is embedded in the outer frame of the liquid immersion objective.

5. The immersion medium supply apparatus according to claim 3, wherein the liquid supply nozzle is embedded in a liquid receiver provided around the forward end of the liquid immersion objective.

6. The immersion medium supply apparatus according to claim 1, further comprising an immersion medium drain unit which drains the immersion medium supplied from the immersion medium supply unit to the liquid immersion objective.

7. The immersion medium supply apparatus according to claim 1, further comprising a sensor which measures a temperature of the immersion medium.

8. The immersion medium supply apparatus according to claim 7, where the sensor is located close to the liquid immersion objective.

9. A fluorescence spectrometry inspection apparatus, comprising:
   a liquid immersion objective which condenses the light from a sample of a fluorescent labeled biological molecule floating in liquid;

an immersion medium which is filled between the sample and the liquid immersion objective;

an optical system comprising a photodetector and a fluorescent illumination to detect a magnified image of at least the liquid immersion objective;

an arithmetic unit which calculates a motion of the sample according to an output from the photodetector;

a monitor which displays a calculation result by the arithmetic unit;

a temperature control unit which controls the immersion medium at a predetermined temperature; and an immersion medium supply unit which supplies the immersion medium objective with the immersion medium controlled at the predetermined temperature by the temperature control unit.

10. The immersion medium supply apparatus according to claim 9, further comprising an immersion medium drain unit which drains the immersion medium supplied from the immersion medium supply unit to the liquid immersion objective.

11. The fluorescence spectrometry inspection apparatus according to claim 9, wherein the arithmetic unit performs operations according to fluorescence correlative spectrometry.

12. The fluorescence spectrometry inspection apparatus according to claim 9, further comprising a sensor which measures the temperature of the immersion medium.

13. The fluorescence spectrometry inspection apparatus according to claim 12, wherein the sensor is located close to the liquid immersion objective.

14. A culture microscope comprising:

a culture vessel which contains a stage on which an observation sample is placed, a microscope which supports the stage, a liquid immersion objective which is supported by the microscope, and an image pickup unit and optics which capture a magnified image of the observation sample set in the microscope;

an immersion medium which is filled between the observation sample and the liquid immersion objective;

a temperature control unit which controls the immersion medium at a predetermined temperature;

an immersion medium supply unit which supplies the immersion medium objective with the immersion medium controlled at the predetermined temperature by the temperature control unit; and an warm air circulator which feeds warm air to the culture vessel.

15. The immersion medium supply unit according to claim 14, further comprising an immersion medium drain unit which drains the immersion medium supplied from the immersion medium supply unit to the liquid immersion objective.

16. The culture microscope according to claim 14, further comprising a sensor which measures the temperature of the immersion medium and the humidity in the culture vessel.

17. The culture microscope according to claim 16, wherein a humidity sensor is located close to the liquid immersion objective.

* * * * *